United States Patent [19]

Sugawara et al.

[11] Patent Number: 5,684,905
[45] Date of Patent: Nov. 4, 1997

[54] FIBER OPTIC PLATE FOR MAKING PATTERN IMAGE INCIDENT ON PHOTOSENSOR

[75] Inventors: Takeo Sugawara; Tsutomu Nagai, both of Hamamatsu, Japan

[73] Assignee: Hamamatsu Phototnics K.K., Hamamatsu, Japan

[21] Appl. No.: 660,574

[22] Filed: Jun. 11, 1996

[30] Foreign Application Priority Data

Jun. 12, 1995 [JP] Japan ................... 7-144758

[51] Int. Cl.⁶ .................................. G02B 6/08
[52] U.S. Cl. .................. 385/120; 385/115; 385/147; 385/901; 362/32
[58] Field of Search .................. 385/115–120, 147, 385/901; 362/32; 356/71

[56] References Cited

U.S. PATENT DOCUMENTS

| 3,402,000 | 9/1968 | Crawford | 385/116 |
| 3,797,910 | 3/1974 | Westwig | 385/120 |
| 3,906,520 | 9/1975 | Phillips | 354/62 |
| 4,932,776 | 6/1990 | Dowiing, Jr. et al. | 356/71 |
| 5,426,296 | 6/1995 | Shikai et al. | 250/227.2 |

FOREIGN PATENT DOCUMENTS

| 4404918 | 8/1994 | Germany . |
| 7-147947 | 7/1995 | Japan . |

*Primary Examiner*—Phan T.H. Palmer
*Attorney, Agent, or Firm*—Cushman Darby & Cushman IP Group of Pillsbury Madison & Sutro LLP

[57] ABSTRACT

The present invention provides a fiber optical plate comprising (i) a first unit formed by a plurality of first optical fibers which are bundled together and include a core portion and a clad portion and (ii) a second unit optically coupled to the first unit and formed by a plurality of second optical fibers which are bundled together and include a core portion, a clad portion, and an optical absorber made of a material for absorbing the light leaking from the clad portion. The first unit has a first input end surface which is inclined with respect to the center axis of the first optical fibers by an angle at which incident light from within air is prevented from being totally reflected by an interface between the core portion and the clad portion of the first optical fibers and a first output end surface which outputs, of light incident on the first input end surface by way of an object in contact with the input end surface, a light component arriving there after being transmitted through the first optical fibers. The second unit has a second input end surface which is bonded to the first output end surface and a second output end surface which outputs, as an optical image, light arriving there after entering the second input end surface and then being transmitted through the second optical fibers.

10 Claims, 7 Drawing Sheets

FIBER OPTIC PLATE FOR MAKING PATTERN IMAGE INCIDENT ON PHOTOSENSOR

BACKGROUND OF THE INVENTION

1. Field of the Invention

The present invention relates to a fiber optical plate unitedly formed as a plurality of optical fibers are bundled together.

2. Related Background Art

Conventionally, as described in U.S. Pat. No. 4,932,776, for example, a fiber optical plate (FOP) in which numerous optical fibers are bundled and united together has been known. A light source is disposed near this FOP such that illumination light enters the FOP toward its input end surface from a tapered section positioned between the input end surface and its output end surface. When a fingertip of a person comes into close contact with this input end face which acts as a detection surface, an irregularity pattern of the surface area of the finger in contact with this input end surface is projected onto the output end surface. As a result, a pattern image of a fingerprint can be read out by CCD (Charge Coupled Device), for example.

SUMMARY OF THE INVENTION

The object of the present invention is to provide a fiber optical plate which can improve the S/N of a pattern image detected after being transmitted from its input end surface to output end surface.

In order to attain the above-mentioned object, the present invention provides a fiber optical plate which is unitedly formed by a plurality of optical fibers bundled together and comprises (i) a first unit formed by a plurality of first optical fibers which are bundled together and include a core portion and a clad portion covering the outer periphery of the core portion and (ii) a second unit optically coupled to the first unit and formed by a plurality of second optical fibers which are bundled together and include a core portion, a clad portion covering the outer periphery of the core portion, and an optical absorber which covers the outer periphery of the clad portion and is made of a material for absorbing the light leaking from the clad portion.

The first unit has a first input end surface which is inclined with respect to the center axis of the plurality of first optical fibers by an angle at which incident light from within air is prevented from being totally reflected by an interface between the core portion and the clad portion of the plurality of first optical fibers and a first output end surface which outputs, of light incident on the first input end surface by way of an object in contact with the first input end surface, a light component arriving there after being transmitted through the plurality of first optical fibers. The second unit has a second input end surface which is bonded to the first output end surface and a second output end surface which outputs, as an optical image, light arriving there after entering the second input end surface and then being transmitted through the plurality of second optical fibers.

In such a fiber optical plate, when the angle of inclination of the first input end surface is set to the condition mentioned above in the first unit, the light which has entered the core portion of the first optical fiber from the input end surface after being propagated through the air is gradually attenuated as being propagated through the core portion, such that it is hardly output from the first output end surface.

Here, when a surface of an object is in close contact with the first input end surface, light transmitted through or reflected by the contact area of the input end surface in contact with this object is transmitted through the core portion of the first optical fiber. Also, a part of the light transmitted through the first unit may leak from the first optical fiber through which it should be transmitted and then may enter its neighboring first optical fiber so as to be transmitted therethrough. Such a light component, which becomes a noise source, may enter the second unit as it is. Since the second optical fiber constituting the second unit has the optical absorber covering the outer periphery of the clad portion, the light which becomes a noise source is absorbed by the optical absorber.

On the other hand, the light transmitted through the first unit includes a light component reflected by the first input end surface with an angle at which the total reflection condition at the interface between the core portion and the clad portion is satisfied. Accordingly, only the light transmitted through or reflected by the contact area is output from the second output end surface of the second unit. Also, light which becomes a noise source is eliminated in the process of being transmitted through the second unit.

Here, preferably, the angle of inclination of the first input end surface is set such that a light-receiving angle 0° is generated for the plurality of first optical fibers based on the critical angle of reflection at which the light incident on the clad portion from the core portion within the plurality of first optical fibers is subjected to total reflection and the critical angle of refraction generated by the light incident on the core portion of the plurality of first optical fibers from within the air at an incident angle of 90°.

Also, preferably, the plurality of the second optical fibers are disposed with their center axis direction coinciding with the center axis direction of the plurality of first optical fibers.

Preferably, the first output end surface is inclined with respect to the center axis direction of the plurality of first optical fibers by an angle which becomes 90° when the angle of inclination of the first input end surface is added thereto.

Also, preferably, the second output end surface is inclined with respect to the center axis direction of the plurality of second optical fibers by an angle which becomes 90° when the angle of inclination of the first input end surface is added thereto.

Preferably, the fiber optical plate of the present invention further comprises a third unit optically coupled to the second unit and formed by a plurality of third optical fibers which are bundled together and include a core portion and a clad portion covering the outer periphery of the core portion, while the third unit has a third input end surface, which is bonded to the second output end surface, and a third output end surface which outputs, as an optical image, light arriving there after entering the third input end surface and then being transmitted through the plurality of third optical fibers, with a diameter which becomes smaller from the third input end surface toward the third output end surface.

Also, preferably, the fiber optical plate of the present invention further comprises a third unit optically coupled to the second unit and formed by a plurality of third optical fibers which are bundled together and include a core portion and a clad portion covering the outer periphery of the core portion, while the third unit has a third input end surface, which is bonded to the second output end surface, and a third output end surface which is inclined with respect to the center axis direction of the plurality of third optical fibers by an angle, which becomes 90° when the angle of inclination of the first input end surface is added thereto, and outputs, as an optical image, light arriving there after entering the third input end surface and then being transmitted through the plurality of third optical fibers.

In this case, desirably, the fiber optical plate of the present invention further comprises a fourth unit optically coupled to the third unit and formed by a plurality of fourth optical fibers which are bundled together and include a core portion and a clad portion covering the outer periphery of the core portion, while the fourth unit has a fourth input end surface, which is bonded to the third output end surface, and a fourth output end surface which outputs, as an optical image, light arriving there after entering the fourth input end surface and then being transmitted through the plurality of fourth optical fibers, with a diameter which becomes smaller from the fourth input end surface toward the fourth output end surface.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DETAILED DESCRIPTION OF THE PREFERRED EMBODIMENTS

In the following, configurations and operations of various embodiments concerning the fiber optical plate of the present invention will be explained in detail with reference to FIGS. 1 to 11. Here, in the explanation of the drawings, constituents identical to each other will be referred to with marks identical to each other without repeating their overlapping explanations. Also, ratios of sizes in the drawings do not always correspond to those in the explanations.

First Embodiment

Figure 1:
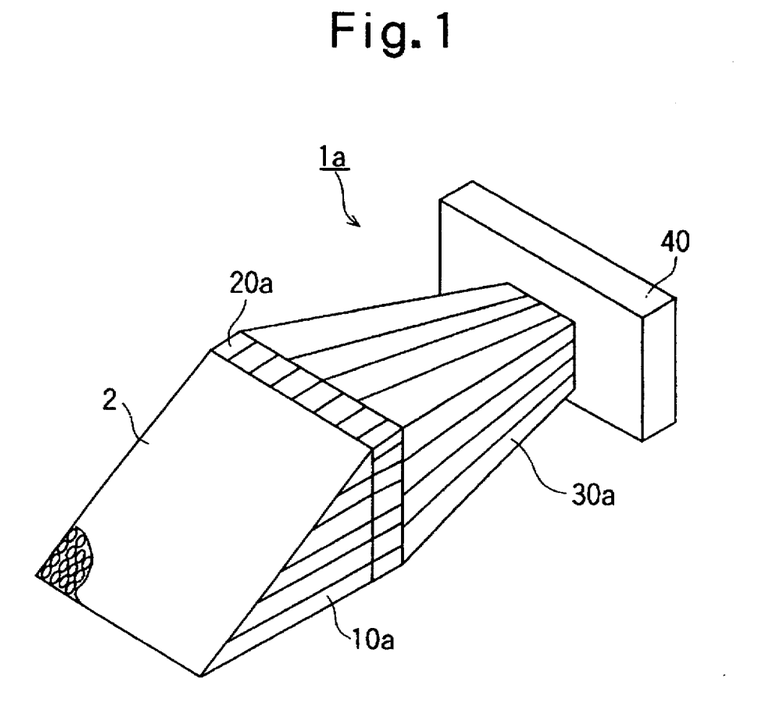
FIG. 1 is a perspective view showing a configuration of a fiber optical plate in accordance with a first embodiment of the present invention.
Figure 2:
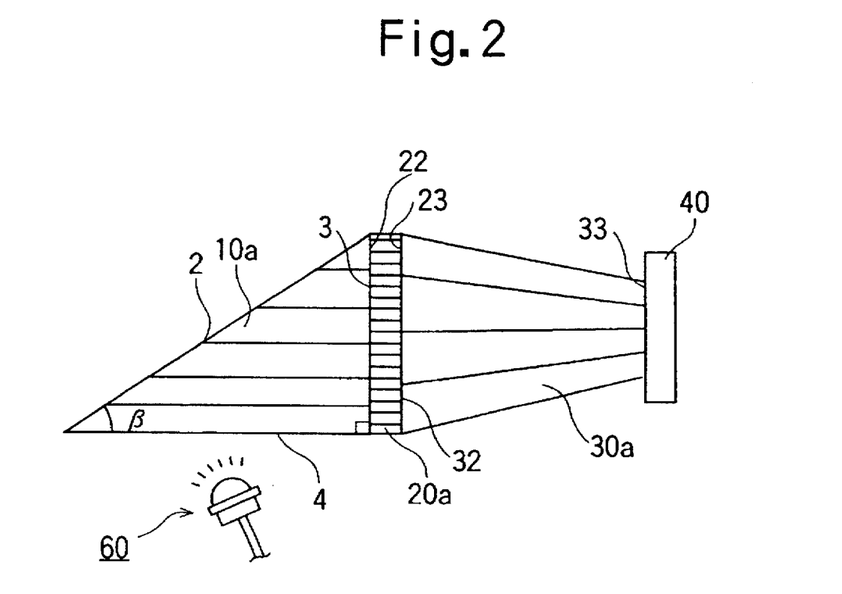
FIG. 2 is a side view showing the configuration of the fiber optical plate of FIG. 1 in detail.

As shown in FIGS. 1 and 2, a fiber optical plate (FOP) $1a$ of this embodiment is used as part of a photosensor section for a fingerprint reader. This FOP $1a$ is constituted by a plurality of units optically coupled to each other in succession along the light advancing direction, such that a slant FOP (slant unit) $10a$, an absorbing FOP (absorbing unit) $20a$, and a tapered FOP (tapered unit) $30a$ are unitedly formed together with their respective end faces being joined to each other. Namely, an output end surface 3 of the slant FOP $10a$ and an input end surface 22 of the absorbing FOP $20a$ are bonded and fixed together by means of a light-transmitting adhesive. An output end surface 23 of the absorbing FOP $20a$ and an input end surface 32 of the tapered FOP $30a$ are bonded and fixed together by means of a light-transmitting adhesive. Here, for convenience, the directions of fibers within various FOPs are indicated by continuous lines in a side surface of the FOP $1a$.

Figure 3:
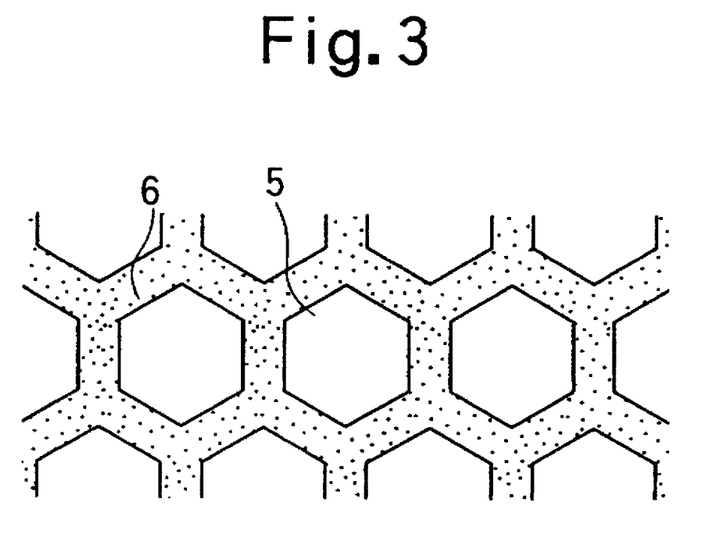
FIG. 3 is an enlarged plan view showing an end surface of the optical fiber section arranged along the input and output end surfaces of a slant FOP or tapered FOP in the fiber optical plate of FIG. 1.

As shown in FIG. 3, the slant FOP $10a$ is unitedly formed by a plurality of optical fibers which are bundled together and comprise a core 5 through which incident light is propagated and a clad 6 covering the outer periphery thereof, while being shaped like a triangle pole as a whole. In this slant FOP $10a$, the output end surface 3 has been cut perpendicular to the optical axis (center axis) of the optical fibers, while its input end surface 2 has been cut with respect to the optical axis (center axis) of the optical fibers at a predetermined angle (slant angle) $\beta$ ($0°<\beta<90°$). This slant angle $\beta$ of the input end surface 2 will be explained in detail later.

Figure 4:
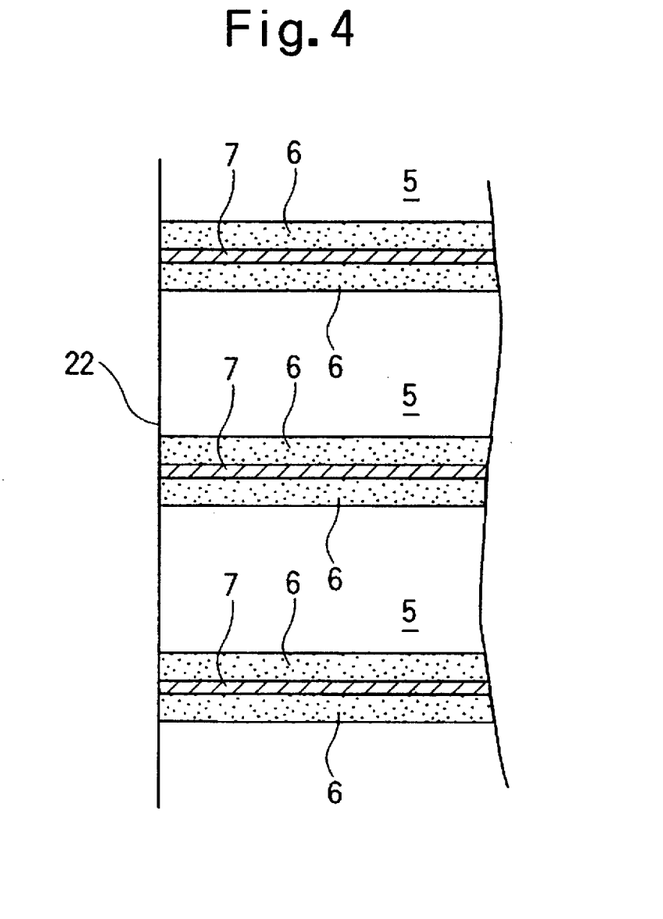
FIG. 4 is an enlarged cross-sectional view showing a partial configuration of an absorbing FOP of the fiber optical plate in FIG. 1 near its input end surface along the light advancing direction.
Figure 5:
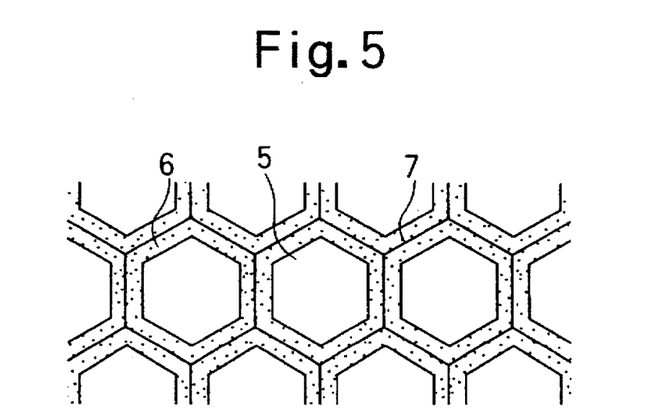
FIG. 5 is an enlarged plan view showing an end surface of the optical fiber section arranged along the input and output end surfaces of the absorbing FOP in the fiber optical plate of FIG. 1.

As shown in FIGS. 4 and 5, the absorbing FOP $20a$ is unitedly formed by a plurality of optical fibers which are bundled together and comprise the core 5 through which incident light is propagated, the clad 6 covering the outer periphery thereof, and an optical absorber 7 covering the outer periphery of the clad 6, while being shaped like a flat plate as a whole. As the optical absorber 7 is disposed at this position, so-called stray light generated by the light leaking from the core 5 and then being propagated through its neighboring optical fiber is absorbed by the optical absorber 7. Accordingly, the neighboring optical fibers are optically insulated from each other by this optical absorber 7.

Also, the input end surface 22 of the FOP $20a$ is bonded to the output end surface 3 of the slant FOP $10a$ so as to be in close contact with each other such that their respective directions of optical fibers are identical to each other. Here, as the optical fiber constituting the FOP $20a$, an optical fiber having an N.A. (numerical aperture) which is the same (or effectively the same) as or smaller than that of the optical fiber constituting the slant FOP $10a$ and a size which is the same as or smaller than that of the latter is used.

As shown in FIG. 3, the tapered FOP $30a$ is unitedly formed by a plurality of optical fibers which are bundled together and comprise the core 5 through which incident light is propagated and the clad 6 covering the outer periphery thereof, while having a taper form in which its diameter continuously reduces from the input end surface 32 toward its output end surface 33. The input end surface 32 of this tapered FOP 30a is bonded to the output end surface 23 of the absorbing FOP 20a. Consequently, an optical image input from the absorbing FOP 20a to the tapered FOP 30a reduces its size as being propagated through the tapered FOP 30a, whereby thus reduced image (object image) is obtained from the output end surface 33 of the tapered FOP 30a. Accordingly, when a light source 60 is disposed so as to face a bottom surface 4 of the slant FOP 10a, a CCD 40 attached to the output end surface 33 of the tapered FOP 30a can detect the reduced image.

Here, the cores 5, clads 6, and optical absorbers 7 in the FOPs 10a, 20a, and 30a are made of respectively common materials. Namely, the core 5 is an F2 glass and has a refractive index of 1.56. The clad 6 is a soda lime glass and has a refractive index of 1.52. The optical absorber 7 is a black glass.

Figure 6:
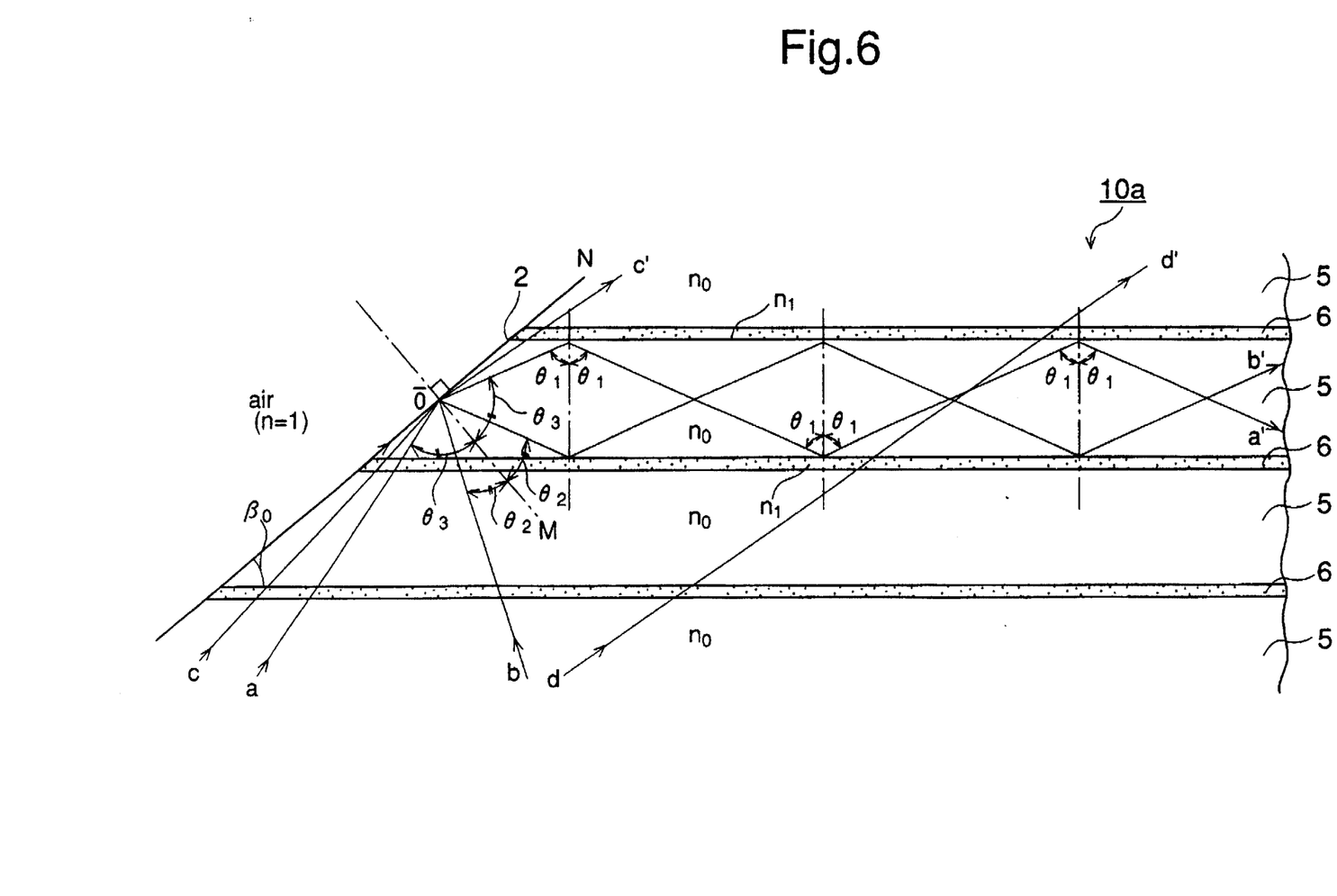
FIG. 6 is an enlarged cross-sectional view showing a partial configuration of the slant FOP in FIG. 1 near its input end surface along the light advancing direction.

FIG. 6 shows a vertical cross section of the slant FOP 10a. In this drawing, $n_0$, $n_1$, and n indicate the refractive index of the core 5, the refractive index of the clad 6, and the refractive index of the air surrounding the slant FOP 10a, respectively. In the slant FOP 10a of this embodiment, the slant angle $\beta$ of the input end surface 2 is defined such that the light-receiving angle becomes 0°. Namely, the slant angle $\beta$ is set to an angle at which no total reflection occurs at the interface between the core 5 and the clad 6 when light is incident thereon at any angle from within the air.

Assuming that the critical angle of reflection at the interface between the core 5 and the clad 6 is $\theta_1$, that the critical angle of refraction at the interface between the air and the core 5 is $\theta_2$, and that the critical angle of reflection at the interface between the air and the core 5 satisfying the critical angle of reflection $\theta_1$ is $\theta_3$, maximum value $\beta_0$ of the slant angle $\beta$ can be determined by the following equations (1) to (4):

$n_0 \sin \theta_1 = n_1 \sin 90°$ [condition for total reflection]  (1)

$n_0 \sin \theta_2 = n \sin 90°$ [condition for light-receiving angle 0°]  (2)

$\beta_0 + (90° + \theta_2) + (90° - \theta_1) = 180°$  (3)

$\theta_3 + \{\beta_0 - (90° - \theta_1)\} = 90°$  (4)

In this case, since $n_0 = 1.56$, $n_1 = 1.52$, and $n=1$, $\theta_1 = 77.0°$, $\theta_2 = 39.9°$, $\theta_3 = 65.9°$, and $\beta_0 = 37.1°$ are determined. Accordingly, it is determined that the slant angle $\beta$ of the input end surface 2 should be set to a value not higher than the $\beta_0$ value of 37.1°.

When, as shown in FIG. 2, the light source 60 is disposed so as to face the lower surface 4 of the slant FOP 10a such that illumination light enters this bottom surface 4 toward the input end surface 2, a light component which enters the clad 6 from the core 5 at an incident angle smaller than the $\theta_1$ value of 77.0° is prevented from being totally reflected by the interface between the core 5 and the clad 6 and thus escapes from the fiber while being refracted.

Here, when the slant angle $\beta$ of the input end surface 2 is set at 35°, in order to satisfy the total reflection condition at the interface between the core 5 and the clad 6, $\theta_2 = 42°$ and $\theta_3 = 68°$ are obtained from the above equations (3) and (4). Namely, the incident angle of the illumination light entering the input end surface 2 should be within the range of 42° to 68°.

Figure 7:
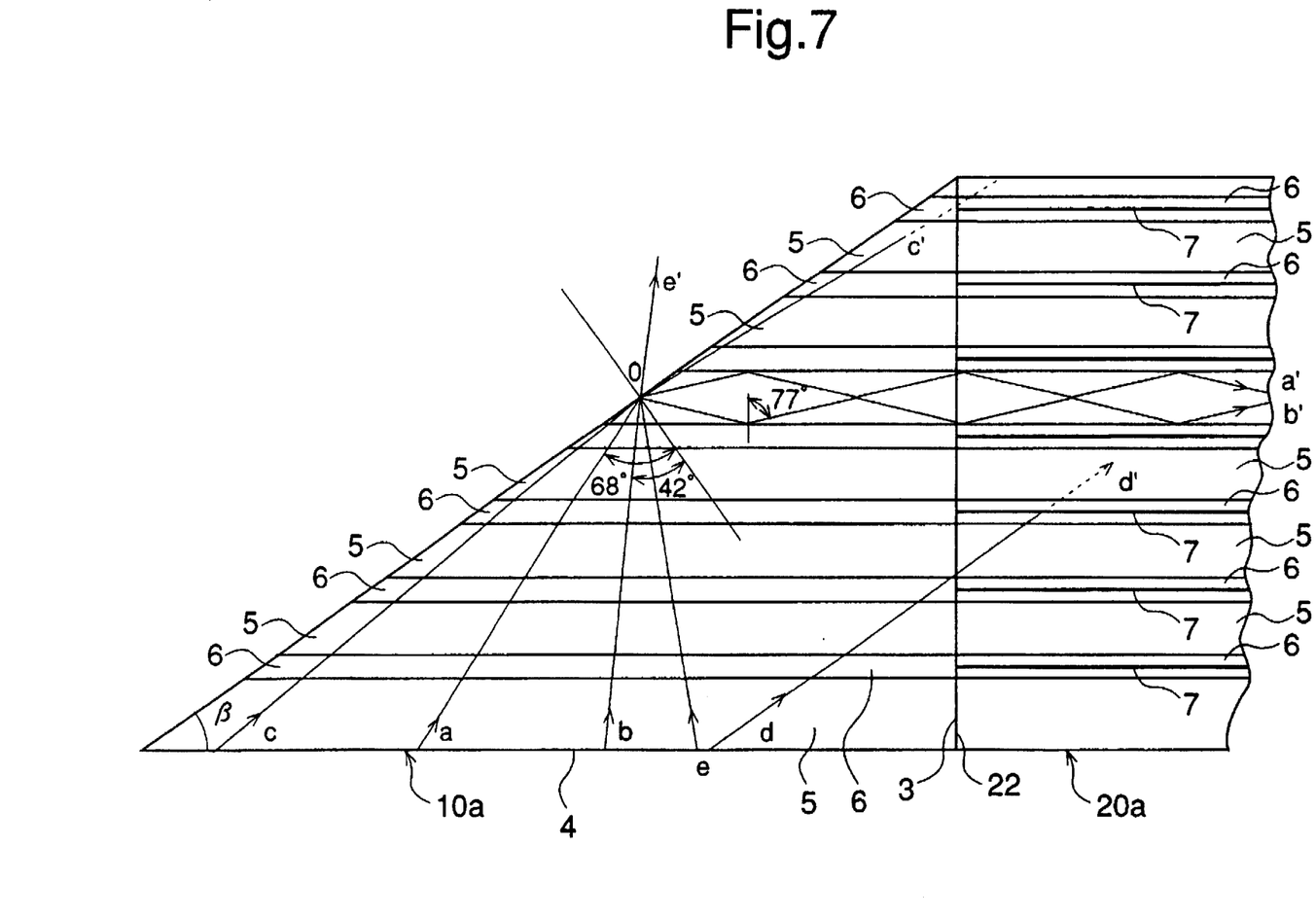
FIG. 7 is an enlarged cross-sectional view showing a partial configuration of the slant FOP and absorbing FOP of the fiber optical plate in FIG. 1 near its input end surface along the light advancing direction.

FIG. 7 shows a vertical cross section of the bonded portion between the slant FOP 10a and the absorbing FOP 20a. The light rays corresponding to the upper and lower limits of the above-mentioned incident angle advance as indicated by lines a–a' and b–b', respectively. The light ray incident on the input end surface 2 at an angle smaller than the angle $\theta_2$ is emitted from the input end surface 2 along a path indicated by line e–e'. The light ray incident on the input end surface 2 at an angle greater than the angle $\theta_3$ is reflected by the input end surface 2 and enters the clad 6 along the path indicated by line c–c'. Since it is incident on the interface between the core 5 and the clad 6 at an angle greater than the angle $\theta_1$, it advances while being repeatedly refracted as it is without being totally reflected by the interface between the core 5 and the clad 6. Here, the illumination light directly emitted toward the output end surface 3 similarly advances along the path indicated by line d–d'.

The light rays represented by these paths c–c' and d–d' are emitted from the side surfaces of the slant FOP 10a to the outside as stray light and then enter the absorbing FOP 20a. In this case, as depicted, they enter the optical absorber 7 of the absorbing FOP 20a and are absorbed thereby so as to be extinguished. Thus, since the stray light propagated through the slant FOP 10a is absorbed and extinguished in the process of being propagated through the absorbing FOP 20a, such stray light is prevented from entering the tapered FOP 30a.

Accordingly, even when the illumination light which has entered the slant FOP 10a from the light source 60 is nearly diffused light, the light output from the output end surface 33 of the tapered FOP 30a does not include a component reflected by the input end surface 2 of the slant FOP 10a other than the signal component. As a result, the object image from which unnecessary light has been eliminated is incident on the CCD 40, whereby an image with an improved S/N is detected.

Second Embodiment

Figure 8:
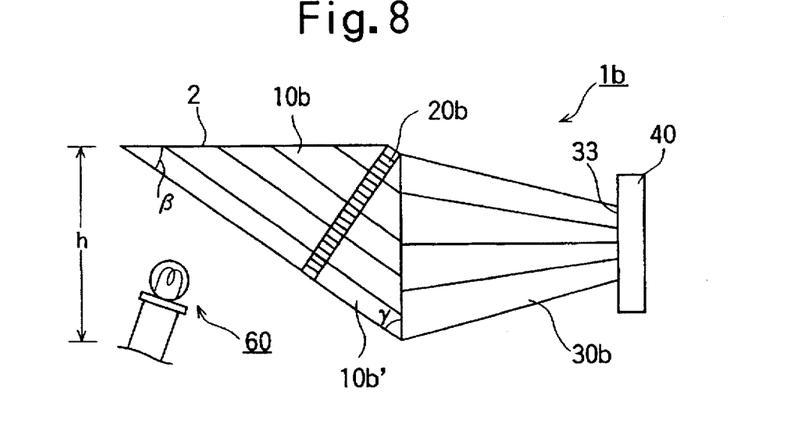
FIG. 8 is a side view showing a configuration of a fiber optical plate in accordance with a second embodiment of the present invention.

As shown in FIG. 8, an FOP 1b of this embodiment is also used as a photosensor of a fingerprint reader or the like. A slant FOP 10b, an absorbing FOP 20b, and a tapered FOP 30b constituting this FOP 1b are formed similar to the slant FOP 10a, the absorbing FOP 20a, and the tapered FOP 30a in the above-mentioned first embodiment, respectively.

In this embodiment, however, unlike the first embodiment, a slant FOP 10b' is unitedly held between the absorbing FOP 20b and the tapered FOP 30b such that their respective end faces are bonded together. Namely, the input end surface of the slant FOP 10b' is fixed to the output end surface of the absorbing FOP 20b by means of a light-transmitting adhesive. The output end surface of the slant FOP 10b' is fixed to the input end surface of the tapered FOP 30b by means of a light-transmitting adhesive.

The slant FOP 10b' positioned at a later stage is formed substantially similar to the slant FOP 10b positioned in a front stage so as to be shaped like a triangle pole as a whole. In this slant FOP 10b', however, contrary to the slant FOP 10b, the input end surface is cut perpendicular to the optical axis of the optical fibers, while the output end surface is cut with respect to the optical axis of the optical fibers at a predetermined slant angle $\gamma = 90° - \beta$ ($0° < \gamma < 90°$).

Therefore, the input end surface 2 of the slant FOP 10b and the output end surface 33 of the tapered FOP 30b are positioned orthogonal to each other. Accordingly, the FOP 1b as a whole can be disposed within a thickness h of the slant FOP 10b, absorbing FOP 20b, and slant FOP 10b' in the normal direction of the input end surface 2.

Third Embodiment

Figure 9:
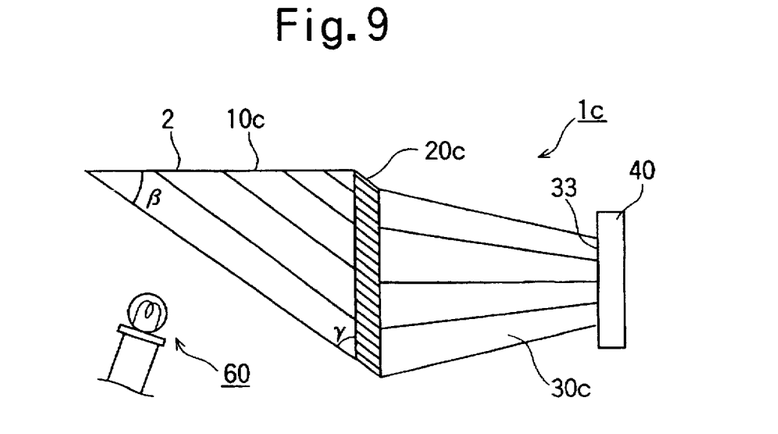
FIG. 9 is a side view showing a configuration of a fiber optical plate in accordance with a third embodiment of the present invention.

As shown in FIG. 9, an FOP 1c of this embodiment is also used as a photosensor of a fingerprint reader or the like. A tapered FOP 30c constituting this FOP 1c is formed similar to the tapered FOP 30a in the above-mentioned first embodiment. However, a slant FOP 10c and an absorbing FOP 20c are configured to be different from the slant FOP 10a and the absorbing FOP 20a in the first embodiment, respectively.

In the slant FOP 10c, unlike the slant FOP 10a, the output end surface is cut with respect to the optical axis of the optical fibers at a predetermined slant angle $\gamma=90°-\beta$ ($0°<\gamma<90°$). Also, in the absorbing FOP 20c, unlike the absorbing FOP 20a, each of the input end surface and output end surface is cut with respect to the optical axis of the optical fibers at the predetermined slant angle $\gamma$. Namely, the absorbing FOP 20c has a parallelogram cross section along the light advancing direction, while having a fiber direction identical to that of the slant FOP 10c.

Therefore, the input end surface 2 of the slant FOP 10c and the output end surface 33 of the tapered FOP 30c are positioned orthogonal to each other. Accordingly, the FOP 1c as a whole can be disposed within the thickness of the slant FOP 10c and absorbing FOP 20c in the normal direction of the input end surface 2.

Fourth Embodiment

Figure 10:
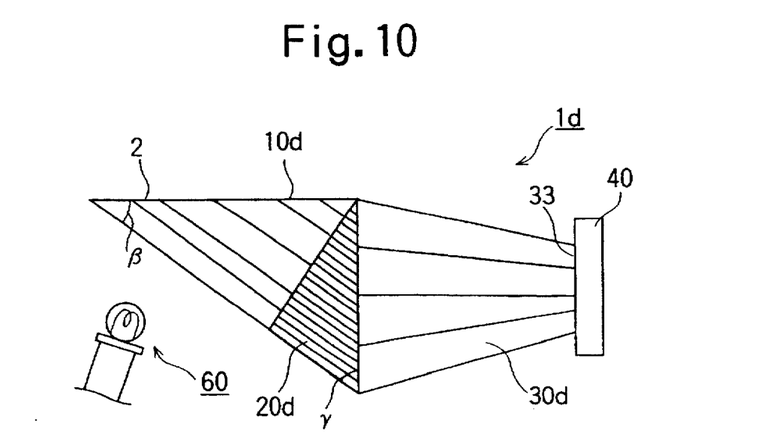
FIG. 10 is a side view showing a configuration of a fiber optical plate in accordance with a fourth embodiment of the present invention.

As shown in FIG. 10, an FOP 1d of this embodiment is also used as a photosensor of a fingerprint reader or the like. A slant FOP 10d and a tapered FOP 30d constituting this FOP 1d are formed similar to the slant FOP 10a and the tapered FOP 30a in the above-mentioned first embodiment. However, an absorbing FOP 20d is configured to be different from the absorbing FOP 20a in the first embodiment.

In the absorbing FOP 20d, unlike the absorbing FOP 20a, the output end surface is cut with respect to the optical axis of the optical fibers at a predetermined slant angle $\gamma=90°-\beta$ ($0°<\gamma<90°$). The absorbing FOP 20d has a right-angled triangular cross section along the light advancing direction, while having a fiber direction identical to that of the slant FOP 10d.

Therefore, the input end surface 2 of the slant FOP 10d and the output end surface 33 of the tapered FOP 30d are positioned orthogonal to each other. Accordingly, the FOP 1d as a whole can be disposed within the thickness of the slant FOP 10d and absorbing FOP 20d in the normal direction of the input end surface 2.

Fifth Embodiment

Figure 11:
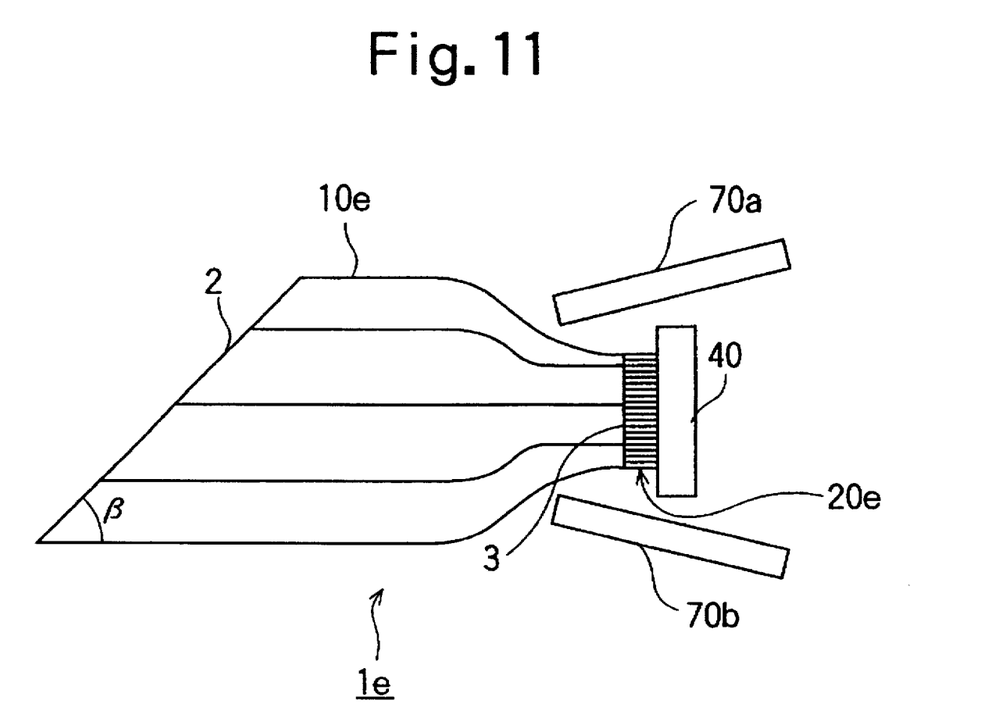
FIG. 11 is a side view showing a configuration of a fiber optical plate in accordance with a fifth embodiment of the present invention.

As shown in FIG. 11, an FOP 1e of this embodiment is also used as a photosensor of a fingerprint reader or the like. An absorbing FOP 20e constituting this FOP 1e is formed similar to the absorbing FOP 20a in the above-mentioned first embodiment. However, its slant FOP 10e is configured so as to have both functions of the slant FOP 10a and tapered FOP 30a in the first embodiment.

Unlike the slant FOP 10a, the slant FOP 10e has a portion with a funnel-like form whose diameter gradually decreases from the input end surface 2 toward the output end surface 3. Also, the light-receiving section of the CCD 40 is bonded to the output end surface 23 of the absorbing FOP 20e. Further, two illumination light sources 70a and 70b are disposed behind the tapered portion of the slant FOP 10e such that illumination light is incident on the input end surface 2 by way of the side surfaces of the slant FOP 10e.

As explained in the foregoing, in the fiber optical plate in accordance with the present invention, the second unit equipped with an optical absorber is disposed at the output end surface of the first unit. Accordingly, even when signal light leaking to the neighboring optical fiber, so-called stray light, is generated in the first unit, such stray light can be eliminated in the second unit. Therefore, the S/N of the output image obtained by way of the second unit can be improved.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Application No. 144758/1995 (7-144758) filed on Jun. 12, 1995 is hereby incorporated by reference.

What is claimed is:

1. A fiber optical plate formed by a plurality of optical fibers bundled together, said fiber optical plate comprising:

a first unit formed by a plurality of first optical fibers which are bundled together and include a core portion and a clad portion covering an outer periphery of said core portion; and a second unit optically coupled to said first unit and formed by a plurality of second optical fibers which are bundled together and include a core portion, a clad portion covering an outer periphery of said core portion, and an optical absorber which covers an outer periphery of said clad portion and is made of a material for absorbing light leaking from said clad portion;

wherein said first unit has a first input end surface which is inclined with respect to center axes of said plurality of first optical fibers by an angle at which incident light from within air is prevented from being totally reflected by an interface between said core portion and said clad portion of said plurality of first optical fibers, and a first output end surface which outputs, of light incident on said first input end surface by way of an object in contact with said first input end surface, a light component arriving there after being transmitted through said plurality of first optical fibers, and wherein said second unit has a second input end surface which is bonded to said first output end surface and inclined with respect to center axes of said plurality of second optical fibers by an angle at which center axis directions of said plurality of second optical fibers coincide with those of said plurality of first optical fibers, and a second output end surface which outputs, as an optical image, light arriving there after entering said second input end surface and then being transmitted through said plurality of second optical fibers.

2. A fiber optical plate according to claim 1, wherein the angle of inclination of said first input end surface is set such that a light-receiving angle 0° is generated for said plurality of first optical fibers based on a critical angle of reflection at which light incident on said clad portion from said core portion within said plurality of first optical fibers is subjected to total reflection and a critical angle of refraction generated by light incident on said core portion of said plurality of first optical fibers from within the air at an incident angle of 90°.

3. A fiber optical plate according to claim 1, further comprising a third unit optically coupled to said second unit and formed by a plurality of third optical fibers which are bundled together and include a core portion and a clad portion covering an outer periphery of said core portion, wherein said third unit has a third input end surface which is bonded to said second output end surface, and a third output end surface which is inclined with respect to center axis directions of said plurality of third optical fibers by an angle, which becomes 90° when the angle of inclination of said first input end surface is added thereto, and outputs, as an optical image, light arriving there after entering said third input end surface and then being transmitted through said plurality of third optical fibers.

4. A fiber optical plate according to claim 1, wherein said first output end surface is inclined with respect to the center axis directions of said plurality of first optical fibers by an angle which becomes 90° when the angle of inclination of said first input end surface is added thereto.

5. A fiber optical plate according to claim 1, wherein said second output end surface is inclined with respect to the center axis directions of said plurality of second optical fibers by an angle which becomes 90° when the angle of inclination of said first input end surface is added thereto.

6. A fiber optical plate according to claim 1, further comprising a third unit optically coupled to said second unit and formed by a plurality of third optical fibers which are bundled together and include a core portion and a clad portion covering an outer periphery of said core portion, wherein said third unit has a third input end surface which is bonded to said second output end surface, and a third output end surface which outputs, as an optical image, light arriving there after entering said third input end surface and then being transmitted through said plurality of third optical fibers, said third unit having a diameter which becomes smaller from said third input end surface toward said third output end surface.

7. A fiber optical plate formed by a plurality of optical fibers bundled together, said fiber optical plate comprising:
   a first unit formed by a plurality of first optical fibers which are bundled together and include a core portion and a clad portion covering an outer periphery of said core portion; and
   a second unit optically coupled to said first unit and formed by a plurality of second optical fibers which are bundled together and include a core portion, a clad portion covering an outer periphery of said core portion, and an optical absorber which covers an outer periphery of said clad portion and is made of a material for absorbing light leaking from said clad portion;
   a third unit optically coupled to said second unit and formed by a plurality of third optical fibers which are bundled together and include a core portion and a clad portion covering an outer periphery of said core portion, wherein said third unit has a third input end surface, which is bonded to said second output end surface and a third output end surface which is inclined with respect to center axis directions of said plurality of third optical fibers by an angle, which becomes 90° when the angle of inclination of said first input end surface is added thereto, and outputs, as an optical image, light arriving there after entering said third input end surface and then being transmitted through said plurality of third optical fibers;
   a fourth unit optically coupled to said third unit and formed by a plurality of fourth optical fibers which are bundled together and include a core portion and a clad portion covering an outer periphery of said core portion, wherein said fourth unit has a fourth input end surface which is bonded to said third output end surface, and a fourth output end surface which outputs, as an optical image, light arriving there after entering said fourth input end surface and then being transmitted through said plurality of fourth optical fibers, said fourth unit having a diameter which becomes smaller from said fourth input end surface toward said fourth output end surface;

wherein said first unit has a first input end surface which is inclined with respect to center axes of said plurality of first optical fibers by an angle at which incident light from within air is prevented from being totally reflected by an interface between said core portion and said clad portion of said plurality of first optical fibers, and a first output end surface which outputs, of light incident on said first input end surface by way of an object in contact with said first input end surface, a light component arriving there after being transmitted through said plurality of first optical fibers, and wherein said second unit has a second input end surface which is bonded to said first output end surface and inclined with respect to center axes of said plurality of second optical fibers by an angle at which center axis directions of said plurality of second optical fibers coincide with those of said plurality of first optical fibers, and a second output end surface which outputs, as an optical image, light arriving there after entering said second input end surface and then being transmitted through said plurality of second optical fibers.

8. A fiber optical plate which is unitedly formed by a plurality of optical fibers bundled together, said fiber optical plate comprising:
   a first unit formed by a plurality of first optical fibers which are bundled together and include a core portion and a clad portion covering an outer periphery of said core portion;
   a second unit optically coupled to said first unit and formed by a plurality of second optical fibers which are bundled together and include a core portion, a clad portion covering an outer periphery of said core portion, and an optical absorber which covers an outer periphery of said clad portion and is made of a material for absorbing light leaking from said clad portion;
   a third unit optically coupled to said second unit and formed by a plurality of third optical fibers which are bundled together and include a core portion and a clad portion covering an outer periphery of said core portion; and
   a fourth unit optically coupled to said third unit and formed by a plurality of forth optical fibers which are bundled together and include a core portion and a clad portion covering an outer periphery of said core portion;

wherein said first unit has a first input end surface which is inclined with respect to center axes of said plurality of first optical fibers by an angle at which incident light from within air is prevented from being totally reflected by an interface between said core portion and said clad portion of said plurality of first optical fibers, and a first output end surface which outputs, of light incident on said first input end surface by way of an object in contact with said first input end surface, a light component arriving there after being transmitted through said plurality of first optical fibers, wherein said second unit has a second input end surface which is bonded to said first output end surface, and a second output end surface which outputs, as an optical image, light arriving there after entering said second input end surface and then being transmitted through said plurality of second optical fibers, wherein said third unit has a third input end surface which is bonded to said second output end surface, and a third output end surface which is inclined with respect to a center axis direction of said plurality of third optical fibers by an angle, which becomes 90° when the angle of inclination of said first input end surface is added thereto, and outputs, as an optical image, light arriving there after entering said third input end surface and then being transmitted through said plurality of third optical fibers, and wherein said fourth unit has a fourth input end surface which is bonded to said third output end surface, and a fourth output end surface which outputs, as an optical image, light arriving there after entering said fourth input end surface and then being transmitted through said plurality of fourth optical fibers, said fourth unit having a diameter which becomes smaller from said fourth input end surface toward said fourth output end surface.

9. A fiber optical plate according to claim 8, wherein said second input end surface is inclined with respect to center axes of said plurality of second optical fibers by an angle which center axis directions of said plurality of second optical fibers coincide with those of said plurality of first optical fibers.

10. A fiber optical plate according to claim 8, wherein the angle of inclination of said first input end surface is set such that a light-receiving angle 0° is generated for said plurality of first optical fibers based on a critical angle of reflection at which light incident on said clad portion from said core portion within said plurality of first optical fibers is subjected to total reflection and a critical angle of refraction generated by light incident on said core portion of said plurality of first optical fibers from within the air at an incident angle of 90°.

* * * * *